United States Patent [19]

Matulic-Adamic

[11] Patent Number: 5,506,349
[45] Date of Patent: Apr. 9, 1996

[54] CHEMICAL SYNTHESIS OF 2', 3'-DIDEOXYCYTIDINE

[75] Inventor: Jasenka Matulic-Adamic, Boulder, Colo.

[73] Assignee: Ribozyme Pharmaceuticals, Inc., Cleveland, Ohio

[21] Appl. No.: 882,479

[22] Filed: May 13, 1992

[51] Int. Cl.$^6$ ....................................... C07H 1/00
[52] U.S. Cl. ..................... 536/28.2; 536/28.5; 536/28.53
[58] Field of Search ............................. 536/23, 27.11, 536/27.14, 28.2, 28.5, 28.53

[56] References Cited

U.S. PATENT DOCUMENTS

| | | | |
|---|---|---|---|
| 4,904,770 | 2/1990 | Starrett, Jr. et al. | 536/28.2 |
| 4,987,224 | 1/1991 | Chu | 536/28.2 |
| 5,084,445 | 1/1992 | Chu et al. | 514/49 |
| 5,099,010 | 3/1992 | Lin et al. | 536/28.2 |

OTHER PUBLICATIONS

Chemical Abstract: 8753h, vol. 110, No. 2, (Jan. 9, 1989).
Gao et al., 51 *J. Org. Chem.* 755, 1986.
Chu et al., 54 *J. Org. Chem.* 2217, 1989.
Sanger et al., 74 *Proc. Natl. Acad. Sci. USA* 5463, 1977.
Herdewijn et al., 31 *J. Med. Chem.* 2040, 1988.
Jain et al., 39 *J. Org. Chem.* 30, 1974.
McCarthy, Jr. et al., 88 *J. Amer. Chem. Soc.* 1549, 1966.
Ludwig and Eckstein, 54 *J. Org. Chem.* 631, 1989.
Bogachev, 13 *Bioorg. Khim.* 1683, 1987.
Samulov and Ofiterov, 9 *Bioorg. Khim.* 52, 1983.
Auer et al., 8 *Nucleosides & Nucleotides* 849, 1989.
Ludwig, 16 *Acta Biochim. Acad. Sci. Hung.* 131, 1981.
Kovacs and Otvos, 29 *Tetrahedron Letters* 4525, 1988.
Kaskar and Markovac, 26 *J. Heterocyclic Chem.* 1531, 1989.
Bhat et al., 9 *Nucleosides & Nucleotides* 1061, 1990.
Starrett, Jr. et al., 9 *Nucleosides & Nucleotides* 885, 1990.
Prisbe and Martin, 15 *Synthetic Communications* 401, 1985.
Huang and Chu, 20 *Synthetic Communications* 1039, 1990.
Holy, 1 *Synthetic Procedure in Nucleic Acid Chemistry* 172, 1968.
Perreault et al., 344 *Nature* 565, 1990.

*Primary Examiner*—Douglas W. Robinson
*Assistant Examiner*—James O. Wilson
*Attorney, Agent, or Firm*—Lyon & Lyon

[57] ABSTRACT

Method for synthesis of 2',3'-dideoxycytidine by providing 5'-silylated-2',3'-dideoxyuridine as an intermediate.

1 Claim, 1 Drawing Sheet

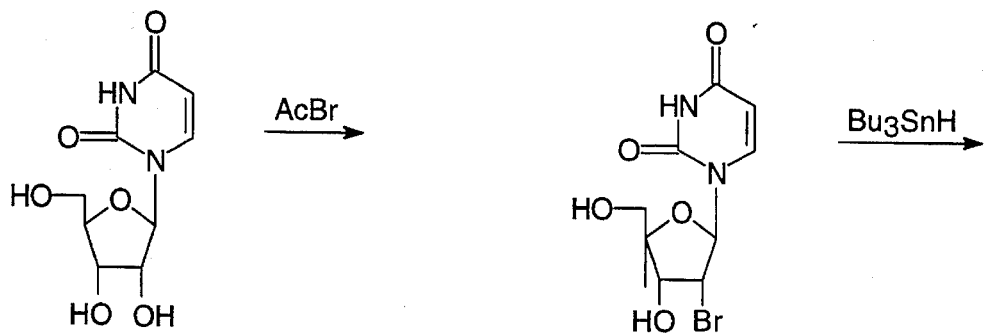
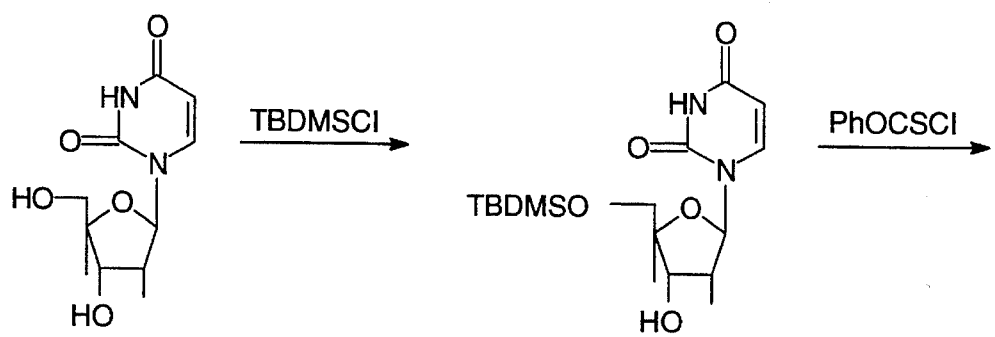
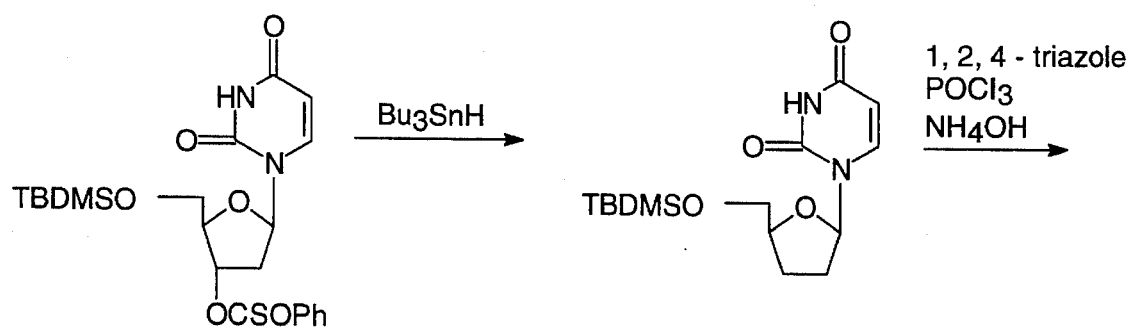
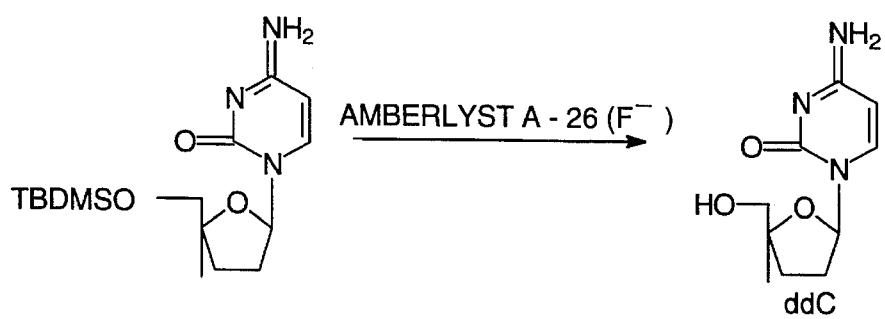

CHEMICAL SYNTHESIS OF 2', 3'-DIDEOXYCYTIDINE

BACKGROUND OF THE INVENTION

This invention relates to the chemical synthesis of 2',3'-dideoxycytidine.

Haoqiang and Chu, 20 *Synth. Commun.* 1039, 1990, describe a method for synthesis of 2'-deoxyuridine using acetyl bromide and HBr and in situ generated tributyltin hydride. Prisbe and Martin, 15 *Synth. Comm.* 401, 1985, describe a method for synthesis of ddC from 2'-deoxycytidine using pivaloyl chloride. Starret et al., 9 *Nucleosides & Nucleotides* 885, 1990, describe a method for synthesis of 2',3'-didehydro-2',3'-dideoxycytidine, and a method for preparation of 2'-bromo-2'-deoxy-3',5'-di-O-acetyl uridine. Bhat et al., 9 *Nucleosides & Nucleotides* 1061, 1990, describe a method for synthesis of 2',3'-dideoxycytidine from 2'-deoxycytidine. Kaskar and Markovac, 26 *J. Heterocycl. Chem.* 1531, 1989, describe a method for synthesis of 2',3'-dideoxycytidine from 2'-deoxycytidine. Chu et al., 54 *J. Org. Chem.* 2217, 1989, describe the synthesis of ddC from cytidine.

SUMMARY OF THE INVENTION

This invention features an improved economical synthetic method for the preparation of dideoxyuridine (ddU) which is then converted into dideoxycytidine (ddC) via a 4-triazolyl intermediate. The method is not only cost efficient, but can be scaled up to several hundred gram quantities. The method generally utilizes inexpensive uridine as a starting material which is converted in a 7 step reaction sequence to ddC with a yield of about 30%.

The ddC can be used for chemical synthesis of sugar-modified nucleosides; chemical synthesis of DNA chain terminators; and chemical synthesis of anti-HIV 2',3'-dideoxynucleosides.

Specifically, the invention features a method for chemical synthesis of 2',3'-dideoxycytidine in which 5'-silylated-2',3'-deoxyuridine is used to form ddC, e.g., by reaction with 1,2,4-triazole, a phosphorusoxychloride, and ammonia, and the silyl group of the resulting product cleaved by use of an ion-exchange resin (specifically, that referred to as the Amberlyst A-26 (F⁻)) and toluene.

Other features and advantages of the invention will be apparent from the following description of the preferred embodiments thereof, and from the claims.

DESCRIPTION OF THE PREFERRED EMBODIMENTS

The drawing will first briefly be described.
Drawing:
The FIGURE is a diagrammatic representation of the chemical synthesis of ddC from uridine by the method of this invention.

Synthesis:
Referring to the FIGURE, in general, 2'-deoxyuridine is formed from uridine by a method similar to that of Haoqiang and Chu, supra, and then converted to ddC by the steps shown.

The following is an example of the synthesis and purification of ddC by the method of this invention. This example is not limiting in the invention and those of ordinary skill in the art will recognize that other equivalent methods can be used to produce the desired chemical.

EXAMPLE

Referring to the FIGURE, uridine (60 g) was treated with acetyl bromide (with or without HBr) in acetonitrile to give 3',5'-di-O-acetyl-2'-bromo-2'-deoxyuridine. The crude material was deoxygenated using tributyltin hydride in the presence of benzoyl peroxide (or 2,2'-azobis-(2-methyl)propionitrile, or azobisisobutyronitrile) to give, after deacetylation with methanolic ammonia, 2'-deoxyuridine in 70% yield. Selective silylation with t-butyldimethylsilyl (TBDMS; triisopropylsilyl chloride or t-butyldiphenylsilyl chloride can be used in place of TBDMS) chloride in pyridine yielded 5'-silylated-2'-deoxyuridine as a crystalline solid in 77% yield. This compound was treated with phenylchlorothionoformate (or 1,1'-thiocarbonyldiimidazole) to give 5'-O-TBDMS-3'-O-phenoxythiocarbonyl-2'-deoxyuridine in 86% yield. Burton deoxygenation of the above derivative with tributyltin hydride (or tributyltin chloride and sodium borohydride) yielded 5'-silylated-2',3'-dideoxyuridine in 77% yield. Reaction of this compound with 1,2,4-triazole and phosphorusoxychloride followed by ammonia treatment afforded 5'-silylated-2'3'-dideoxycytidine in 88% yield. Cleavage of the 5'-silyl group using ion-exchange resin Amberlyst A-26 (F⁻) (a macroreticular quaternary ammonium resin, 20–60 mesh particle size) in refluxing toluene gave 2',3'-dideoxycytidine (ddC) in 99% yield. The overall yield (from uridine) was 31%.

Other embodiments are within the following claims.

I claim:

1. Method for synthesis of 2',3'-dideoxycytidine comprising the steps of reacting 5'-silylated-2',3'-deoxyuridine with 1,2,4-triazole and phosphorusoxychloride and ammonia to yield 5'-silylated-2',3'-dideoxycytidine cleaving the 5'-silylated group of said 5'-silylated-2',3'-dideoxycytidine with an ion exchange resin wherein said ion exchange resin is a macroreticular quaternary ammonium resin with 20–60 mesh particle size, in the presence of toluene to yield said 2',3'-dideoxycytidine.

* * * * *